United States Patent
Berrada et al.

(10) Patent No.: US 9,790,538 B2
(45) Date of Patent: Oct. 17, 2017

(54) ALKALINE ACTIVATION FOR IMMOBILIZATION OF DNA TAGGANTS

(71) Applicant: APDN (B.V.I) INC., Tortola (VG)

(72) Inventors: Abdelkrim Berrada, Lake Ronkonkoma, NY (US); MingHwa Benjamin Liang, East Setauket, NY (US); Lawrence Jung, Forest Hills, NY (US); Kurt Jensen, Stony Brook, NY (US)

(73) Assignee: APDN (B.V.I.) INC., Road Town, Tortola (VG)

(*) Notice: Subject to any disclaimer, the term of this patent is extended or adjusted under 35 U.S.C. 154(b) by 0 days.

(21) Appl. No.: 13/789,093

(22) Filed: Mar. 7, 2013

(65) Prior Publication Data

US 2014/0256881 A1 Sep. 11, 2014

(51) Int. Cl.
C12Q 1/68 (2006.01)

(52) U.S. Cl.
CPC .................. *C12Q 1/6802* (2013.01)

(58) Field of Classification Search
None
See application file for complete search history.

(56) References Cited

U.S. PATENT DOCUMENTS

| | | | |
|---|---|---|---|
| 4,183,989 A | 1/1980 | Tooth | |
| 4,278,557 A | 7/1981 | Elwell, Jr. | |
| 4,454,171 A | 6/1984 | Diggle, Jr. | |
| 4,548,955 A * | 10/1985 | Okahata | A61K 9/1272 521/53 |
| 4,739,044 A | 4/1988 | Stabinsky | |
| 4,757,141 A | 7/1988 | Fung et al. | |
| 5,047,519 A | 9/1991 | Hobbs, Jr. et al. | |
| 5,089,691 A | 2/1992 | Morisaki et al. | |
| 5,132,242 A | 7/1992 | Cheung | |
| 5,139,812 A | 8/1992 | Lebacq | |
| 5,151,507 A | 9/1992 | Hobbs, Jr. et al. | |
| 5,429,952 A | 7/1995 | Garner et al. | |
| 5,451,505 A | 9/1995 | Dollinger | |
| 5,498,283 A | 3/1996 | Botros et al. | |
| 5,595,871 A | 1/1997 | DelVecchio et al. | |
| 5,599,578 A | 2/1997 | Butland | |
| 5,602,381 A | 2/1997 | Hoshino et al. | |
| 5,639,603 A | 6/1997 | Dower et al. | |
| 5,643,728 A | 7/1997 | Slater et al. | |
| 5,763,176 A | 6/1998 | Slater et al. | |
| 5,776,713 A | 7/1998 | Garner et al. | |
| 5,866,336 A | 2/1999 | Nazarenko et al. | |
| 5,942,444 A | 8/1999 | Rittenburg et al. | |
| 5,989,823 A | 11/1999 | Jayasena et al. | |
| 6,013,789 A | 1/2000 | Rampal | |
| 6,030,657 A | 2/2000 | Butland et al. | |
| 6,057,370 A | 5/2000 | Weiland et al. | |
| 6,127,120 A | 10/2000 | Graham et al. | |
| 6,140,075 A | 10/2000 | Russell et al. | |
| 6,169,174 B1 | 1/2001 | Hasegawa et al. | |
| 6,261,809 B1 | 7/2001 | Bertling et al. | |
| 6,312,911 B1 | 11/2001 | Bancroft et al. | |
| 6,342,359 B1 | 1/2002 | Lee et al. | |
| 6,399,397 B1 | 6/2002 | Zarling et al. | |
| 6,576,422 B1 | 6/2003 | Weinstein et al. | |
| 6,686,149 B1 | 2/2004 | Sanchis et al. | |
| 6,703,228 B1 * | 3/2004 | Landers | C12Q 1/6827 435/6.11 |
| 6,743,640 B2 | 6/2004 | Whitten et al. | |
| 6,995,256 B1 | 2/2006 | Li et al. | |
| 7,031,927 B1 | 4/2006 | Beck et al. | |
| 7,060,874 B2 | 6/2006 | Wilkins | |
| 7,115,301 B2 | 10/2006 | Sheu et al. | |
| 7,160,996 B1 | 1/2007 | Cook | |
| 7,223,906 B2 | 5/2007 | Davis | |
| 7,250,195 B1 | 7/2007 | Storey et al. | |
| 7,732,492 B2 | 6/2010 | Makino et al. | |
| 8,278,807 B2 | 10/2012 | Agneray et al. | |
| 9,266,370 B2 | 2/2016 | Jung et al. | |
| 9,297,032 B2 | 3/2016 | Jung | |
| 2001/0039018 A1 * | 11/2001 | Matson et al. | 435/6 |

(Continued)

FOREIGN PATENT DOCUMENTS

EP 0 477 220 B1 4/1992
EP 0 623 658 A2 11/1994

(Continued)

OTHER PUBLICATIONS

M. Ageno, E. Dore and C. Frontali The Alkaline Denaturation of DNA, Biophys. J. Nov. 1969, 9(11): 1281. Abstract.
S. Hou, X. Li and X-Z Feng Method to improve DNA Condesation Efficiency by Alkali Treatment. Nucleosides, Nucleotides and Nucleic Acids, 2009. 28:725-735.Taylor & Francis Group, LLC.
M. Ageno, E. Dore and C. Frontali The Alkaline Denaturation of DNA, Biophys. J. Nov. 1969, 9(11): 1281-1311.
T. Thiel, L. Liczkowski and S.T. Bissen New zwitterionic butanesulfonic acids that extend the alkaline range of four families of good buffers: Evaluation for use in biological Systems. J. Biochem. Biophys. Methods (1998) 37: 117-129. Elsevier.

(Continued)

*Primary Examiner* — Robert T Crow
(74) *Attorney, Agent, or Firm* — Hoffmann & Baron, LLP

(57) ABSTRACT

The invention provides methods for stably binding and immobilizing deoxyribonucleic acid onto objects and substrates. The method includes exposing the deoxyribonucleic acid to alkaline conditions, and contacting the deoxyribonucleic acid to the object or substrate. The alkaline conditions are produced by mixing the deoxyribonucleic acid with an alkaline solution having a pH of about 9.0 or higher, and contacting the deoxyribonucleic acid to the substrate. The immobilized DNA can be used as a taggant and can be used in combination with other detectable taggants, such as optical reporters. Methods for authentication of a DNA marked object are also provided.

4 Claims, 8 Drawing Sheets

(56) References Cited

U.S. PATENT DOCUMENTS

| | | |
|---|---|---|
| 2002/0048822 A1 | 4/2002 | Rittenburg et al. |
| 2002/0064639 A1 | 5/2002 | Rearick |
| 2002/0119485 A1 | 8/2002 | Morgan |
| 2002/0128234 A1 | 9/2002 | Hubbell et al. |
| 2002/0129251 A1 | 9/2002 | Itakura |
| 2002/0137893 A1* | 9/2002 | Burton et al. .............. 530/350 |
| 2002/0160360 A1* | 10/2002 | Chenchik et al. .............. 435/6 |
| 2002/0167161 A1 | 11/2002 | Butland |
| 2002/0187263 A1 | 12/2002 | Sheu et al. |
| 2003/0096273 A1* | 5/2003 | Gagna .................. C12Q 1/6834 435/6.12 |
| 2003/0142704 A1 | 7/2003 | Lawandy |
| 2003/0142713 A1 | 7/2003 | Lawandy |
| 2003/0162296 A1 | 8/2003 | Lawandy |
| 2003/0177095 A1 | 9/2003 | Zorab et al. |
| 2004/0063117 A1 | 4/2004 | Rancien et al. |
| 2004/0071718 A1* | 4/2004 | Tsai ........................ A61K 39/35 424/185.1 |
| 2004/0166520 A1 | 8/2004 | Connolly |
| 2004/0219287 A1 | 11/2004 | Regan et al. |
| 2005/0059059 A1 | 3/2005 | Liang |
| 2005/0112610 A1 | 5/2005 | Lee |
| 2005/0214532 A1 | 9/2005 | Kosak et al. |
| 2006/0017957 A1 | 1/2006 | Degott et al. |
| 2006/0017959 A1 | 1/2006 | Downer et al. |
| 2006/0117465 A1 | 6/2006 | Willows et al. |
| 2006/0121181 A1 | 6/2006 | Sleat et al. |
| 2006/0286569 A1 | 12/2006 | Bar-Or et al. |
| 2007/0012784 A1 | 1/2007 | Mercolino |
| 2007/0048761 A1 | 3/2007 | Reep et al. |
| 2007/0072197 A1 | 3/2007 | Rayms-Keller et al. |
| 2007/0117119 A1 | 5/2007 | Akita et al. |
| 2007/0254292 A1* | 11/2007 | Fukasawa et al. .............. 435/6 |
| 2008/0081357 A1 | 4/2008 | Kwon et al. |
| 2008/0153135 A1 | 6/2008 | Liu |
| 2008/0216255 A1 | 9/2008 | Poovey et al. |
| 2008/0293052 A1 | 11/2008 | Liang et al. |
| 2009/0069199 A1 | 3/2009 | Brandenburg |
| 2009/0075261 A1 | 3/2009 | Hayward et al. |
| 2009/0136163 A1* | 5/2009 | Kerr ........................ B65D 31/10 383/120 |
| 2009/0253127 A1 | 10/2009 | Gaudreau et al. |
| 2009/0286250 A1 | 11/2009 | Hayward |
| 2009/0311555 A1 | 12/2009 | Badyal et al. |
| 2010/0050344 A1 | 3/2010 | Peltz et al. |
| 2010/0075407 A1 | 3/2010 | Duffy et al. |
| 2010/0285447 A1* | 11/2010 | Walsh et al. .............. 435/5 |
| 2010/0285490 A1 | 11/2010 | Dees et al. |
| 2010/0285985 A1 | 11/2010 | Liang et al. |
| 2010/0307120 A1 | 12/2010 | Stover |
| 2011/0229881 A1 | 9/2011 | Oshima |
| 2011/0250594 A1 | 10/2011 | Liang et al. |
| 2012/0264742 A1* | 10/2012 | Furuishi .............. A61K 9/0014 514/216 |
| 2013/0048731 A1 | 2/2013 | Flickner et al. |
| 2014/0256881 A1 | 9/2014 | Berrada et al. |
| 2014/0272097 A1 | 9/2014 | Jung et al. |
| 2015/0018538 A1 | 1/2015 | Berrada et al. |
| 2016/0168781 A1 | 6/2016 | Tran et al. |

FOREIGN PATENT DOCUMENTS

| | | |
|---|---|---|
| EP | 0840350 A2 | 5/1998 |
| EP | 140333 A1 | 3/2004 |
| EP | 2444136 | 4/2012 |
| GB | 2434570 A1 | 8/2007 |
| JP | S63503242 A | 11/1988 |
| RU | 2084535 C | 7/1997 |
| RU | 2170084 C1 | 7/2001 |
| WO | 8706383 A1 | 10/1987 |
| WO | 90/14441 A1 | 11/1990 |
| WO | 9506249 A1 | 3/1994 |
| WO | 9502702 A1 | 1/1995 |
| WO | 9745539 A1 | 12/1997 |
| WO | 9806084 A1 | 2/1998 |
| WO | 9959011 A1 | 11/1999 |
| WO | 0055609 A1 | 9/2000 |
| WO | 0125002 A1 | 4/2001 |
| WO | 0136676 | 5/2001 |
| WO | 0199063 A1 | 12/2001 |
| WO | 02057548 A1 | 7/2002 |
| WO | 02084617 A1 | 10/2002 |
| WO | 03030129 A2 | 4/2003 |
| WO | 03/080931 A1 | 10/2003 |
| WO | 2004025562 A1 | 3/2004 |
| WO | 2007078833 A | 7/2007 |
| WO | 2008154931 A | 12/2008 |
| WO | 2010075858 A1 | 3/2010 |
| WO | WO2013154943 A1 | 10/2013 |
| WO | 2013170009 A1 | 11/2013 |
| WO | WO2014062754 A1 | 4/2014 |

OTHER PUBLICATIONS

Versalift, "Market Growth, the evolution of the aerial lift industry," Oct. 1, 2002. Accessed on web Nov. 10, 2008.

Schulz et al., "Archived or directly swabbed latent fingerprints as a DNA source for STR typing," Forensic Science International, 127 (2002) 128-130.

Zuckermann, et al. "Efficient methods for attachment of thiol specific probes to the 3' end of synthetic oligonucleotides." Nucleic Acids Research, vol. 15, pp. 5305-5321 (1987) IRL Press Limited, Oxford.

Whitcombe, et al. "Detection of PCR products using self-probing amplicons and fluorescence," Nature Biotechnology, vol. 17 pp. 804-807 (1999) Nature America, Inc. New York.

Tyagi, et al. Multicolor molecular beacons for allele discrimination, Nature Biotechnology, vol. 16, pp. 49-53 (1998) Nature Publishing Group, New York.

Nazarenko, et al. "A closed tube format for amplification and detection of DNA based on energy transfer," Nucleic Acids Research, vol. 25, pp. 2516-2521 (1997) Oxford University Press.

Tyagi & Kramer, "Molecular Beacons: Probes that Fluoresce upon Hybridization" nature Biotechnology, vol. 14, pp. 303-308 (1996) Nature Publishing Group, New York.

Sproat, et al. "The synthesis of protected 5'-mercapto-2',5'-didoexyribonucleoside-3-O-phosphoramidites, uses of 5'-mercapto-didoexyribonucleosides." Nucleic Acids Research, vol. 15, pp. 4837-4848 (1987) IRL Press Limited, Oxford.

Nelson, "Bifunctional oligonucleotide probes synthesized using a novel CPG support are able to detect single base pair mutations." Nucleic Acids Research, vol. 17, pp. 7187-7194 (1989) IRL Press Limited, Oxford.

Gupta, et al. "A general method for the synthesis of 3'-sulfhydryl and phosphate group containing oligonucleotides." Nucleic Acids Research, vol. 19, pp. 3019-3025 (1991) Oxford University Press, Oxford, England.

Lee, et al. "Allelic discrimination by nick translation PCR with fluorescent probes." Nucleic Acids Research, vol. 21, pp. 3761-3766 (1993) Oxford University Press, Oxford, England.

Holland, et al. "Detection of specific polymerase chain reaction product by utilizing the 5' [to] 3' exonuclease activity of Thermus aquaticus DNA polymerase." Proceedings of the National Academy of Sciences, USA vol. 86 pp. 7276-7280 (1991) National Academy of Sciences, Washington, DC.

Heid, et al. "Real Time Quantitative PCR." Genome Research, vol. 6, pp. 986-994 (1996) Cold Spring Harbor Laboratory Press, Woodbury, New York.

Gibson, et al. "A Novel Method for Real Time Quantitative RT-PCR" Genome Research, vol. 6, pp. 995-1001 (1996) Cold Spring Harbor Laboratory Press, Woodbury, New York.

Agrawal & Tang, "Site-specific functionalization of oligodoexynucleotides for non-radioactive labelling." Tetrahedron Letters, vol. 31, pp. 1543-1546 (1990) Pergamon Press, Great Britain.

(56) References Cited

OTHER PUBLICATIONS

Van Der Rijke, et al. "Up-converting phosphor reporters for nucleic acid microarrays." Nature Biotechnology, vol. 19, pp. 273-276 (2001) Nature Publishing Group, New York.

Corstjens, et al. "Infrared Up-converting phosphors for bioassays." IEE Proceedings—Nanobiotechnology, vol. 152, pp. 64-72 (2005) Institution of Engineering and Technology, London.

Hussein et al. "Molecular Characterization of Cotton Genotypes Using PCR-based Markers." Journal of Applied Sciences Research 3(10) 1156-1169 (2007). INSInet Publication.

Jiang, et al. "Polyploid formatioopn created unique avenues for response to selection in *Gossypium* (cotton)" Proceedings of the National Academy of Sciences, USA vol. 95 pp. 4419-4424 (1998) National Academy of Sciences, Washington, DC.

Lee, et al. "The complete genome sequence of Gossypium hursutum, organization and phylogenetic relationships to other angiosperms." BMC Genomics 7:61, Mar. 2006.

Ibrahim, et al. Complete nucleotide sequence of the cotton (*Gossypium barbadense* L.) chloroplast genome with a comparative analysis of sequence among 9 dicot plants. Genes and Genetic Systems vol. 81. pp. 311-321 (2006).

Kaneda, S. et al. Modification of the glass surface property in PDMS-glass hybrid microfluidoc devces. Analytical Sciences, Jan. 2012, vol. 28, No. 1, pp. 39-44.

Hosokawa, K. et al. DNA Detection on a power-free microchip with laminar flow-assisted dendritic amplification. Analytical Sciences, 2010, Vo. 26, No. 10, pp. 1052-1057.

Park, H. et al. Stress response of fibroblasts adherent to the surface of plasma-treated poly(lactic-co-glucolic acid) nanofiber matrices. Colloids surf B Biointerfaces, May 2010, 1; 77(1):90-95.

Tuzlakoglu K. et al. A new route to produce starch-based fiber mesh scaffolds by wet spinning and subsequent surface modification as a way to improve cell attachment and proliferation. J Biomed Mater Res A, Jan. 2010, 92 (1):369-377.

Karahan et al., Fibers and Polymers, vol. 9, pp. 21-26 (2008).

Ullrich, T. et al. Competitive reporter monitored amplification (CMA)-quantification of molecular targets by real time monitoring of competitive reporter hybridization. PLoS One, 2012, vol. 7, No. 4 E35438. doi;l0.1371/journal.pone.0035438, p. 1-13.

Instant Krazy Glue, product description, accessed website Feb. 24, 2012, 4 pages.

Supplementary European Search Report for corresponding European Application No. EP14820538, pp. 1-8 (Jan. 17, 2017).

* cited by examiner

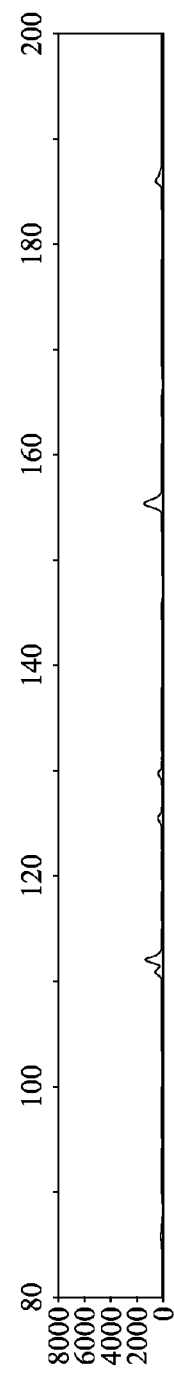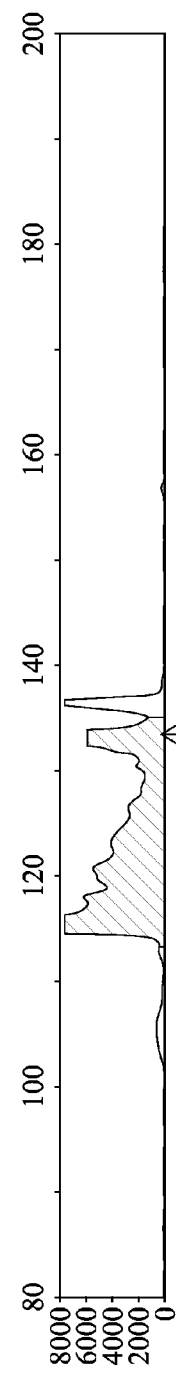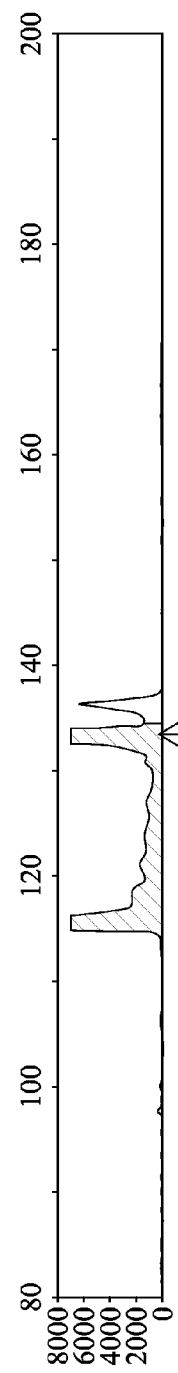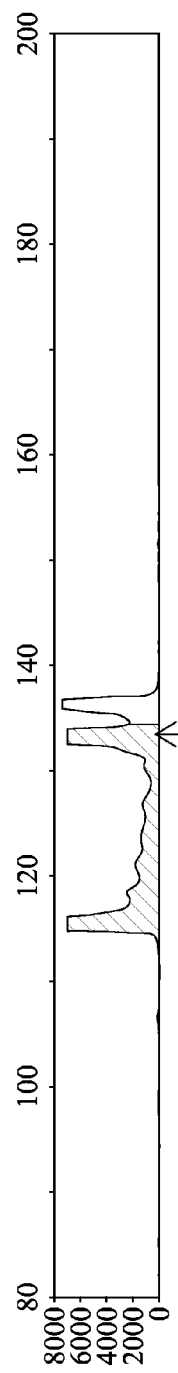

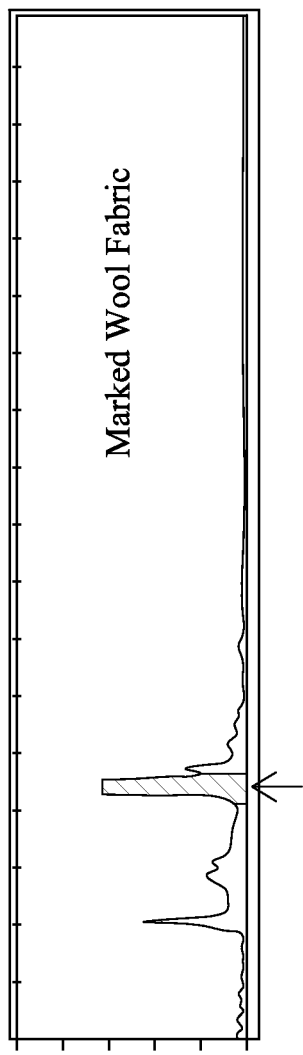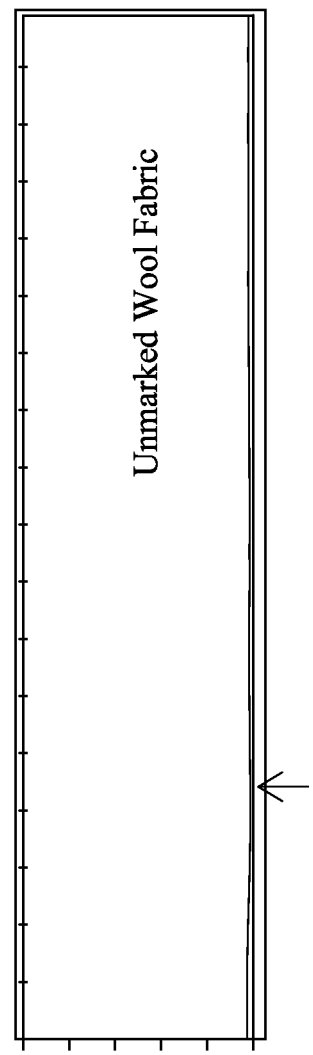

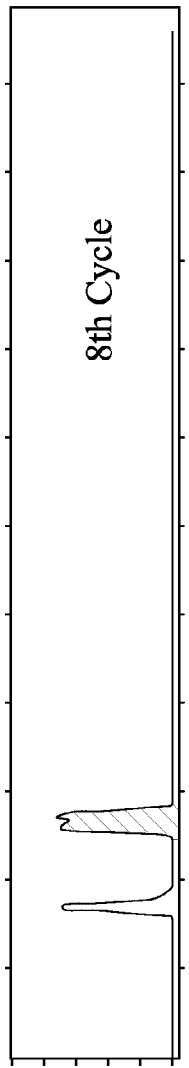
FIG. 6C  8th Cycle
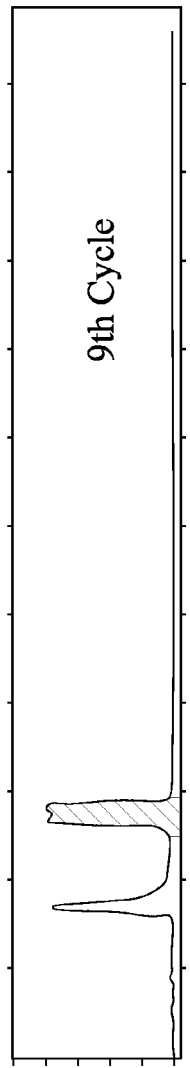
FIG. 6D  9th Cycle
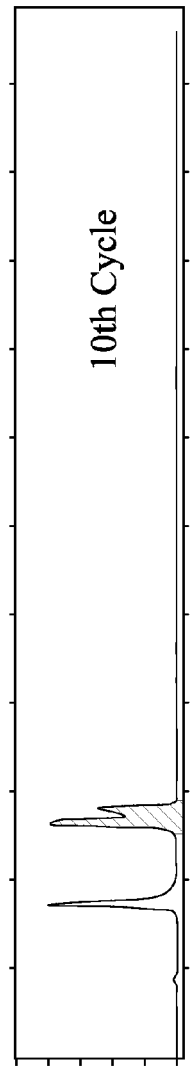
FIG. 6E  10th Cycle

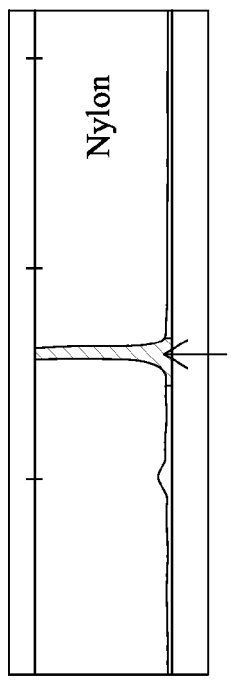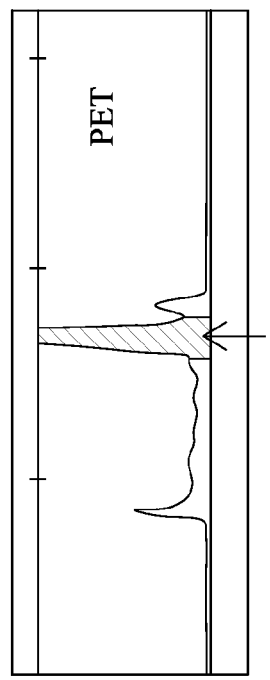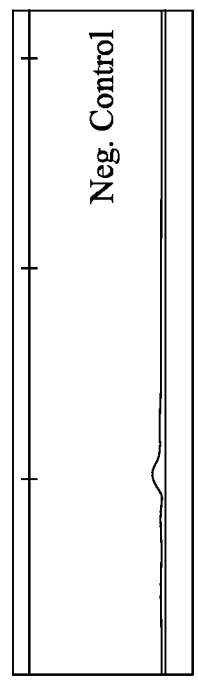

ALKALINE ACTIVATION FOR IMMOBILIZATION OF DNA TAGGANTS

TECHNICAL FIELD

The present invention relates to methods for facilitating the stable binding and immobilization of traceable DNA taggants onto the surface of an object, or for inclusion into liquids containing dyes and inks that can be applied to an object such that the taggant can be bound and subsequently detected and the object authenticated.

BACKGROUND

Counterfeiting and blending of high-end products with cheaper material has become a major liability problem for major brand names. The International Chamber of Commerce (ICC) reported that in 2008, counterfeited goods resulted in a loss of $650 billion in revenues and 2.5 million jobs. The ICC projected that the loss in revenues will exceed $1.7 trillion in 2015, which is equivalent to 2% of the world economy. In addition to the revenue losses, certain counterfeit products were linked directly to serious health and safety issues. The counterfeit goods have infiltrated most industries from textiles to microchips, and even pharmaceuticals.

Counterfeiting has become a serious problem, spreading throughout many different industries all around the world. It was estimated that about $600 billion worth of counterfeited goods enter the market on a yearly basis (Cattaui, 2012). Products including pharmaceuticals, toys, entertainment products, clothing, fashion accessories, money, electronics, and any other products of value have imitation counterfeits in the market for consumers. The problem with counterfeits is that they not only hurt the name of the original and the economy, but because these products are not coming from reliable sources, their quality and efficacy could be compromised. Counterfeiting often has minimal consequences on those distributing the fake goods, compared to the deadly consequences that could result from the malfunctioning of products with counterfeit components. In 2011, VisionTech of Clearwater, Fla. was one of the few companies actually charged for the sale of counterfeit chips, after thousands of these fake chips had been sold to all sectors of the electronics industry.

Counterfeiting pharmaceuticals has also become a giant industry within the United States. These fake drugs can be extremely dangerous as there is no precision or consistency required to sell them. By using real or similar drugs to pass the initial testing, these counterfeiters can later sell products with a variety of different ingredients, without the knowledge of the consumer. A trend of global increase in medicine purchased online has made it easier to sell counterfeit pharmaceuticals. These counterfeits have made up 70% of the drug supply in nations such as China and India, leading to many more deaths all over the world, as these nations supply drugs to many other countries (See Chakraborty, FoxBusiness, June 2012). In April of 2012, a drug called Avastin, a cancer drug, was imitated. " . . . 120 phony vials were purchased in Turkey under the name Alzutan and shipped through Britain by U.K.-based middlemen in a strikingly similar shipment pattern as the fakes that first hit U.S. doctors' offices in February." These counterfeit drugs are sold for high profits, with low penalties, making this process attractive for criminals. This has become a multi-billion dollar industry, with an estimate of reaching $100 billion dollars within the next decade (Chakraborty). This could pose some serious health risks for consumers, who will gravitate towards the cheaper products, which are unknowingly counterfeits, making them susceptible to these fakes.

Another industry that has been invaded with counterfeit products is the electronics industry. Other than the well-known counterfeiting of standard music players and phones, products such as microchips have also been counterfeited. This is a major predicament because a customer of these products is the United States Department of Defense (DoD). Counterfeit microchips from the far east have made their way into the Navy and the Pentagon's weapons systems (Kelley, Business Insider, Military & Defense). These counterfeit manufacturers first develop products that function like the original to pass the initial testing, but then manufacture inferior, cheaper products, while still selling them as the original. Once they enter the weapons stream, the counterfeits are incredibly difficult to detect, and due to their unreliability, higher product failure has resulted, leaving a large vulnerability in national defense. Not only could these products fail, but access to faulty microchips within United States' weapons systems from unauthorized sources, could allow access into American communications without detection (Kelley).

Cases of counterfeit microchips mostly go unreported, with no consequences to those in the supplier chain, as companies are reticent to associate themselves with the fakes and risk the fallout from acknowledging that their systems may be compromised. In the case of the THAAD (Terminal High-Altitude Area Defense) system, a U.S. military program, they disclosed that their system was compromised in a way to protect themselves from future counterfeit parts and to raise awareness to the issue plaguing these systems. This system was developed to take down missiles in flight, requiring a high degree of precision, which could be jeopardized by a malfunction in any one of its chips. These counterfeit microchips, mainly purchased from Far Eastern sources, are frequently commercial-grade products that are not capable of withstanding the environment that military equipment must endure, meaning that equipment could cease to function abruptly, leading to disastrous consequences.

A new mandate, Section 818, with the National Defense Authorization Act for Fiscal Year 2012 has been created in support of measures to protect against counterfeiting. This mandate requires companies selling parts or products to the United States government to have anti-counterfeiting measures in place. These include inspecting and authenticating their products before they are sold. The mandate also holds suppliers responsible for the counterfeit products they supply, including the costs and legal ramifications of any damage that occurs due to the faulty products. Until this mandate was added to the National Defense Authorization Act, there had been no legal consequences for providing counterfeit products to consumers and no enforced monitoring or detection system required.

The risk involved with counterfeiting has forced many companies to act on their own to find ways to protect their products and set up anti-counterfeiting methods. One of the approaches used is to add a fluorophore to the products, to be able to visually detect which products are legitimate. A fluorophore is a chemical compound that fluoresces or re-emits light of a longer wavelength upon being excited with light. This occurs as a molecule within the fluorophore is excited causing the molecule to emit photons and fluoresce. The fluorophore can serve as a dye or a marker for these products, which can be applied during the early stages of production.

This method, although effective at first, no longer protects products as counterfeiters have copied the products along with the fluorophore. Counterfeiters were able to extract the fluorophore from the product, duplicate it, and add to their counterfeit products, making the product fluoresce under UV light just as the real product would. This has created a need for an anti-counterfeiting method by which products can be forensically authenticated which is secure and cannot be duplicated by the counterfeiters themselves. One method that the US Military is now looking into is the use of DNA to mark authentic products. DNA, with specific sequences, is incorporated into these products through the means of ink or other materials. This can then be detected under a UV light, with the way the material fluoresces. The specific DNA sequences are virtually impossible to duplicate, making counterfeiting impossible. This DNA would be impossible to remove as it would be embedded throughout the entire material.

Nucleic Acids as Security Markers

Despite being composed of relatively simple nucleotide building blocks, nucleic acids are capable of encoding a vast array of information: for instance, the human genome encodes all the information necessary for the synthesis and assembly of all the components of the human body from the neural networks of the brain to the intricate structures of the skeleton, tissues and organs. Nucleic acids include deoxyribonucleic acid (DNA) and the more labile ribonucleic (RNA). Nucleic acid sequences can be unique and complex and utilization of these particular characteristics in solving several common coding problems, such as authenticating and tracking products and detecting counterfeit products, has recently attracted great interest.

Many product manufacturers utilize apparent qualities and definitive designs identifiable as "trade dress" to uniquely identify their high quality and high value products and thereby earn the trust of their customers. Others also add labels for anti-counterfeit purposes. Traditional anti-counterfeiting labels are generally formed from materials having particularly targeted physical or chemical characteristics, for example, magnetic strips on checkbooks, laser holographs on credit cards, fluorescent ink on stock certificates, and heat-sensitive inks on confidential documents. Anti-counterfeiting labels have also been made by adding specific antigens to objects that need to be identified, the antigens can then be detected with an antibody specific for the antigen. However, antigens and antibodies are proteins with characteristically poor stability under many environmental conditions of temperature and humidity, and are prone to denaturation or even degradation and consequently lose activity and can easily be destroyed, thereby reducing the accuracy and reliability of identification.

Thus, nucleic acids, such as, for example, deoxyribonucleic acid (DNA) and ribonucleic acid (RNA) which encode essential hereditary information have been looked to as an improved alternative to commonly used anti-counterfeiting labels and markers. DNA and RNA are polymers consisting of a chain of nucleotides, referred to as "oligonucleotides" consisting of relatively short chains of up to say, twenty to fifty bases in length, or "polynucleotides" for longer chains. These oligonucleotide or polynucleotide chains consist of a number of nucleotides linked together in sequence like beads on a string. Each nucleotide consists of a ribose sugar-phosphate linked to one of only four kinds of nitrogenous bases: adenine (often represented in abbreviated form as "A"), guanine (represented as "G"), cytosine (represented as "C") and thymine (represented as "T") in the case of DNA; and adenine (A), guanine (G), cytosine (C) and uracil (U) in the case of RNA. The oligonucleotides or polynucleotides share the same sugar-phosphate backbone. The 3'-hydroxyl group of the ribose sugar of one nucleotide is covalently bonded to the 5'-phosphate group of its neighboring nucleotide to form a chain structure with each of the planar nitrogenous bases protruding from the chain not unlike the teeth of a comb.

The bases A, T, G and C in one oligonucleotides or polynucleotides chain are each capable of specific-pairing with another base a different chain to form a double stranded structure, or with the same chain to form a double stranded loop or hairpin structure: Adenine specifically bonds with thymine through two hydrogen bonds in DNA (or with uracil in RNA) and cytosine specifically bonds with guanine through three hydrogen bonds. That is, T will bond to A and G to C bringing two nucleotide chains together to form a double strand, or two parts of a single nucleotide chain together to form a double stranded region with each strand of the duplex connected by a loop.

An additional advantage of nucleic acids for use as markers or taggants is that with the appropriate proper protection these molecules can be preserved for long periods of time. Evidence from preserved specimens in glaciers, ice sheets, tar pits and bogs and marshes shows that DNA is resilient to degradation over thousands, and in some cases millions of years. Such evidence has been used to deduce information concerning the ancestry and origins of ancient peoples as well as of plants and animals. Protected marker DNA can also be stabilized in polymers for coating of high value articles or objects of interest so as to survive long periods of time and can then used for identification, authentication and tracking purposes. This ability to persist over long periods of time coupled with very sensitive methods to detect low numbers of molecules for instance by amplification using the polymerase chain reaction (PCR), makes nucleic acids, and DNA in particular, an attractive candidate for use as a marker. Moreover, nucleic acids offer an almost unlimited coding capacity since the number of possible unique sequences increases fourfold with every additional base of the sequence of the oligonucleotide or polynucleotide.

There is a need in the art for a system permitting efficient, stable and detectable marking of an article, particularly an article of value with DNA taggants for the purposes of identification, authentication, tracking and validation. There is a need to protect brand names, to easily and rapidly detect counterfeited products and provide forensic evidence to assist in the prosecution of counterfeiters.

SUMMARY

The present invention provides methods of immobilizing a deoxyribonucleic acid to a substrate or of binding a deoxyribonucleic acid to a substrate. The method includes exposing the deoxyribonucleic acid to alkaline pH, and contacting the alkaline exposed deoxyribonucleic acid to the substrate.

One embodiment of the present invention provides a method of binding of a deoxyribonucleic acid to a substrate, wherein the method includes exposing the deoxyribonucleic acid to alkaline conditions wherein the alkaline conditions are produced by mixing the deoxyribonucleic acid with an alkaline solution having a high pH (such as for instance a pH of about 9.0 to about 14.0), and contacting the alkaline-exposed deoxyribonucleic acid to the substrate. In one embodiment, the alkaline solution is a solution of a hydroxide of an alkali metal.

In another embodiment of the present invention, the alkaline solution is a solution of a high pH buffer. In another embodiment, the high pH buffer is selected from the group consisting of CABS (4-[cyclohexylamino]-1-butanesulphonic acid), CAPS (N-cyclohexyl-3-amino-propanesulfonic acid), AMP (2-amino-2-methyl-1-propanol), CAPSO (N-cyclohexyl-2-hydroxyl-3-aminopropanesulfonic acid), CHES (2-(N cyclohexylamino) ethanesulphonic acid), AMPSO (3-[(1,1-dimethyl-2-hydroxyethyl)amino]-2-hydroxypropanesulfonic acid) and a mixture of any two or more of the foregoing.

In another embodiment, an object marked with marker DNA in which the marker DNA is an alkaline pH activated DNA bound to the object is provided In another embodiment, the alkaline pH activated DNA is bound to a material selected from the group consisting of cotton, wool, nylon, plastic, metal, glass, wood, printing ink and a pharmaceutical composition.

In an embodiment, the object marked with the marker DNA includes one of a pharmaceutical tablet, a pharmaceutical capsule, or a pharmaceutical powder.

BRIEF DESCRIPTION OF THE FIGURES

FIG. 1: Marking and authentication of Giza 86 cotton. FIG. 1A: Shows a background DNA analysis of Giza 86. FIG. 1B: Authentication of Giza 86 cotton after DNA marking. FIGS. 1C and 1D: Authentication of Giza 86 cotton after washing.

FIG. 2: Marking and authentication of Giza 88 cotton.

FIG. 3: Marking and authentication of Giza 86 cotton.

FIG. 4: Marking and authentication of Giza 88 cotton.

FIG. 5: Marking of wool yarn and authentication of fished fabric. Yarn was marked with SigNature™ DNA, woven, and professionally finished. SigNature™ DNA was recovered and authenticated. FIG. 5A: Authentication of finished fabric. FIG. 5B: Identical authentication procedure carried out on unmarked fabric.

FIG. 6: Authentication of fabric marked with SigNature™ DNA after a series of ten dry cleanings: Yarn was marked with SigNature™ DNA, the fabric was woven, finished professionally, and subjected to 10 cycles of dry cleaning. FIGS. 6A-E are authentications after fabrics were dry cleaned 6, 7, 8, 9, and 10 times, respectively.

FIG. 7: Master batches of nylon (FIG. 7A) and PET (FIG. 7B) pellets were mixed with SigNature™ DNA, extruded, and resulting yarns and films were washed. FIG. 7C shows a control without DNA. The final products were authenticated as described.

DETAILED DESCRIPTION

Figure 2A:
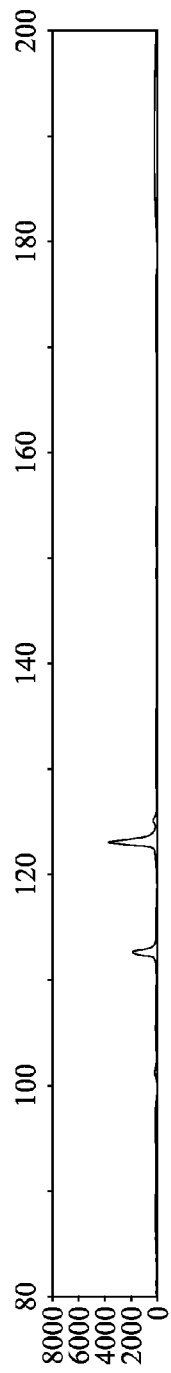
FIG. 2A: Shows a background DNA analysis of Giza 88 cotton.
Figure 2B:
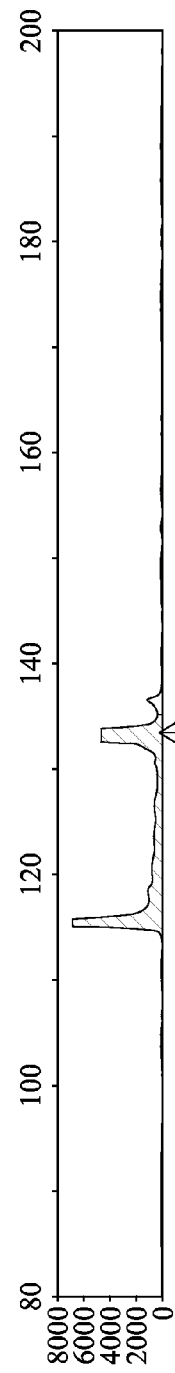
FIG. 2B: Authentication of Giza 86 cotton after DNA marking.
Figure 2C:
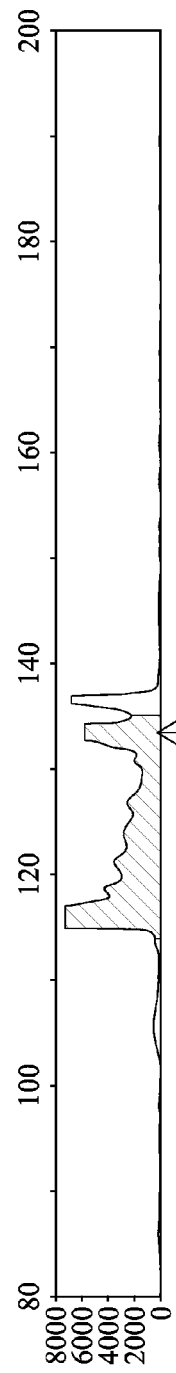
FIGS. 2C and 2D: Authentication of Giza 88 cotton after washing.
Figure 2D:
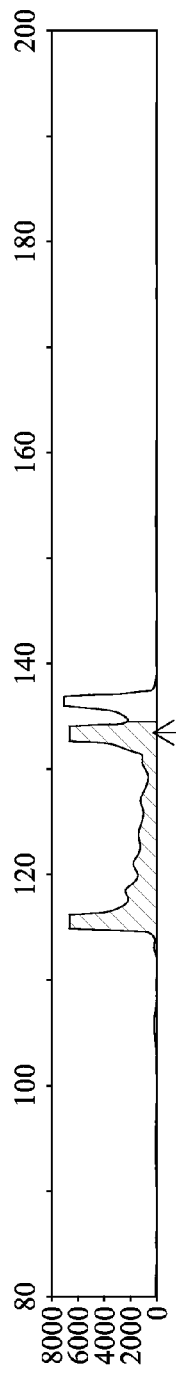
Figure 3A:
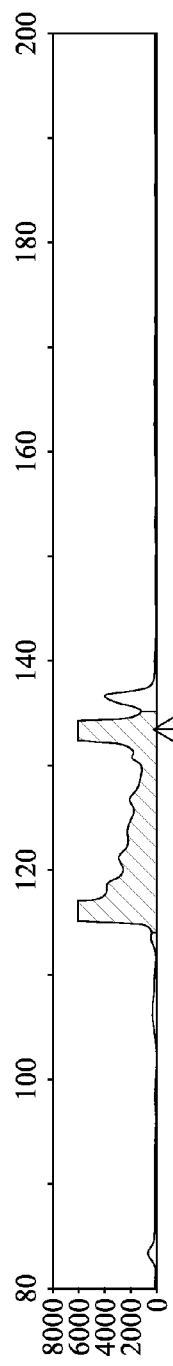
FIG. 3A: Authentication of Giza 86 cotton before washing.
Figure 3B:
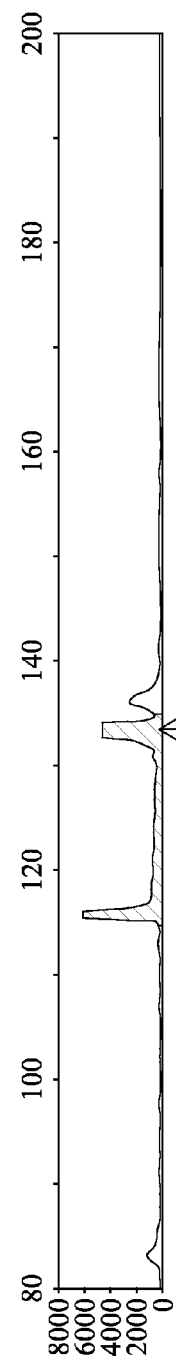
FIG. 3B: Authentication of Giza 86 cotton after water washing.
Figure 3C:
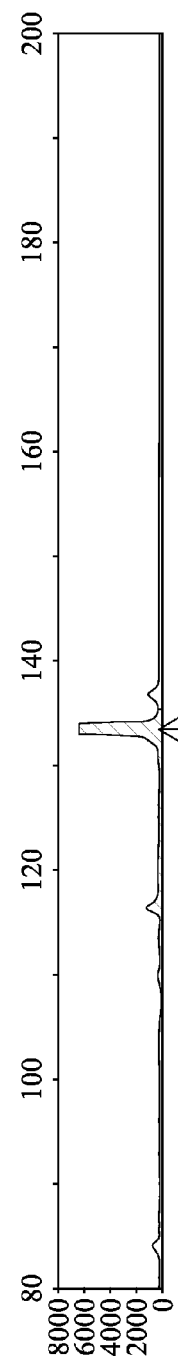
FIG. 3C: Authentication of Giza 86 cotton after sequential water and alcohol washing.
Figure 3D:
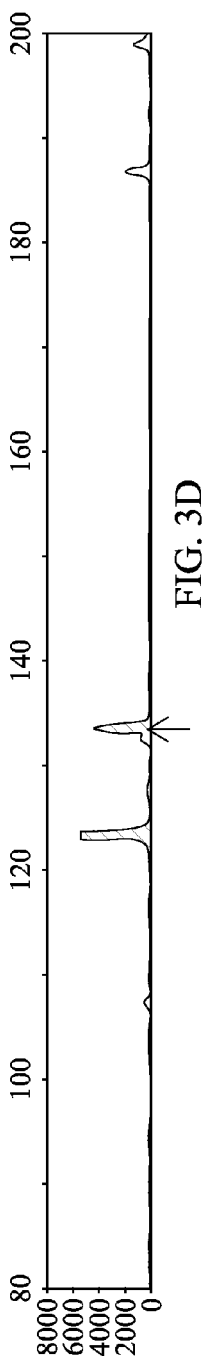
FIG. 3D: Authentication of Giza 86 cotton after sequential water, alcohol, and solvent washing.
Figure 4A:
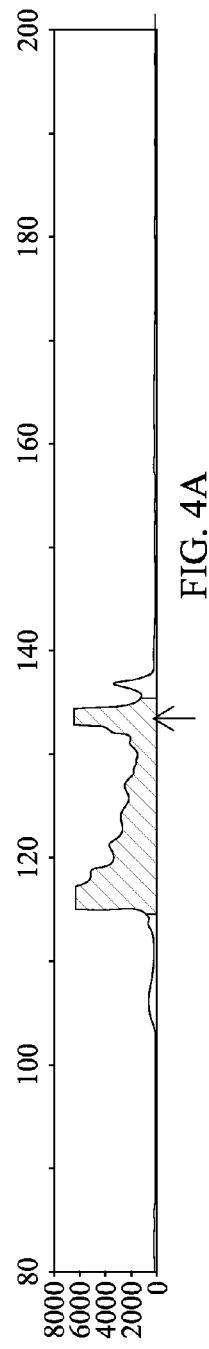
FIG. 4A: Authentication of Giza 88 cotton before washing.
Figure 4B:
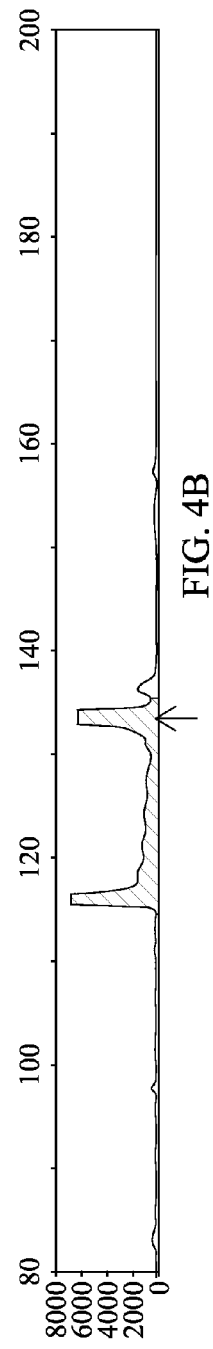
FIG. 4B: Authentication of Giza 88 cotton after water washing.
Figure 4C:
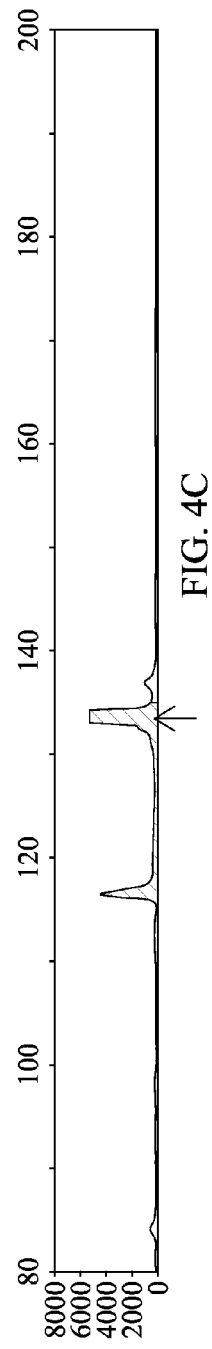
FIG. 4C: Authentication of Giza 88 cotton after sequential water and alcohol washing.
Figure 4D:
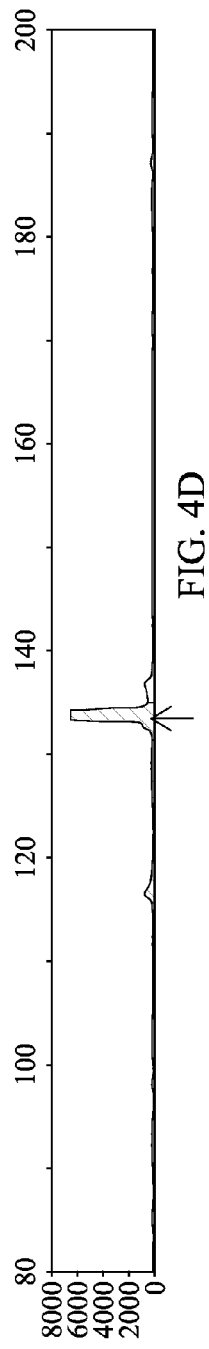
FIG. 4D: Authentication of Giza 88 cotton after sequential water, alcohol, and solvent washing.

Definitions:

As used herein, the terms "binding to a substrate" and "immobilizing" are interchangeable as applied to DNA binding and immobilization.

The term "taggant" as used herein denotes a DNA marker, and optionally the DNA marker can be in combination with a second marker substance. The marker DNA and the additional one or more markers, when present are affixed to an object to indicate a property of the object, such as for instance its source of manufacture. The object to be marked with the taggant can be any solid traceable item, such as an electronic device, an item of clothing, paper, fiber, or fabric, or any other item of commerce, or cash or valuables, whether in storage or in transit. Alternatively, the item of commerce to be marked with the taggant can be a liquid, such as for instance an ink, a dye or a spray. In another alternative, the item of commerce can be a commodity item, such as paper, metal, wood, a plastic or a powder. The taggant can be, for example, specific to the company or the type of item (e.g. a model number), specific to a particular lot or batch of the item (lot number), or specific to the actual item, as in, for instance, a serial number unique to the item. In addition, the taggant can indicate any one or more of a variety of other useful items of data; for example, the taggant can encode data that indicates the name and contact information of the company that manufactured the tagged product or item, the date of manufacture, the distributor and/or the intended retailer of the product or item. The taggant can also indicate, for example and without limitation, component data, such as the source of the component incorporated into the item or the identity of the production plant or machinery that was used in the manufacture of the product or item; the date that the product or item was placed into the stream of commerce, the date of acceptance by the distributor and/or the date of delivery to the retailer and any other useful commercial, or other data such as for instance personal information of the owner of a custom made item. Each element of data or indicia can be encrypted or encoded in the taggant and can be deciphered from taggant recovered from the object and decoded or decrypted according to the methods described herein. The decoded or decrypted data can then be used to verify the properties of the object, or to authenticate the object, or to exclude counterfeit items.

The term "PCR" refers to a polymerase chain reaction. PCR is an amplification technology useful to expand the number of copies of a template nucleic acid sequence via a temperature cycling through melting, re-annealing and polymerization cycles with pairs of short primer oligonucleotides complementary to specific sequences bordering the template nucleic acid sequence in the presence of a DNA polymerase, preferably a thermostable DNA polymerase such as the thermostable Taq polymerase originally isolated from the thermophillic bacterium (*Thermus aquaticus*). PCR includes but is not limited to standard PCR methods, where in DNA strands are copied to provide a million or more copies of the original DNA strands (e.g. PCR using random primers: See for instance *PCR with Arbitrary Primers: Approach with Care*. W. C. Black IV, Ins. Mol. Biol. 2: 1-6, December 2007); Real-time PCR technology, wherein the amount of PCR products can be monitored at each cycle (*Real time quantitative PCR*: C. A. Heid, J. Stevens, K. J. Livak and P. M. Williams, 1996 Genome Research 6: 986-994); Reverse transcription-PCR wherein RNA is first copied in DNA stands and thereafter the DNA strands are amplified by standard PCR reactions (See for example:

*Quantitative RT-PCR: Pitfalls and Potential*: W. F. Freeman, S. J. Walker and K. E. Vrana; BioTechniques 26:112-125, January 1999).

The term "monomer" as used herein refers to any chemical entity that can be covalently linked to one or more other such entities to form an oligomer or a polymer. Examples of "monomers" include nucleotides, amino acids, saccharides, amino acids, and the like.

The term "nucleic acid" means a polymer composed of nucleotides which can be deoxyribonucleotides or ribonucleotides. These compounds can be natural or synthetically produced deoxyribonucleotides or ribonucleotides. The synthetically produced nucleic acid can be of a naturally occurring sequence, or a non-natural unique sequence.

The terms "ribonucleic acid" and "RNA" denote a polymer composed of ribonucleotides. The terms "deoxyribonucleic acid" and "DNA" denote a polymer composed of deoxyribonucleotides.

The term "nucleotide" means a monomeric unit comprising a sugar phosphate, usually ribose-5'-phosphate or 2'-deoxyribose-5'-phosphate covalently bonded to a nitrogen-containing base, usually, adenine (A), guanine (G), cytosine (C), or thymine (T) in the case of a deoxyribonucleotide, and usually, adenine (A), guanine (G), cytosine (C), or uracil (U) in the case of ribonucleotides.

The term "oligonucleotide" as used in this specification refers to single or double stranded polymer composed of covalently nucleotide monomers forming a chain of from two to about twenty nucleotides in length.

The term "polynucleotide" as used in this specification refers to single or double stranded polymer composed of covalently nucleotide monomers forming a chain of generally greater than about twenty nucleotides in length.

Nucleic acids having a naturally occurring sequence can hybridize with nucleic acids in a sequence specific manner. That is they can participate in hybridization reactions in which the complementary base pairs A:T (adenine:thymine) and G:C (guanine:cytosine) form intermolecular (or intramolecular) hydrogen bonds and cooperative stacking interactions between the planar neighboring bases in each strand through Pi electrons, together known as Watson-Crick base pairing interactions. The bases of the nucleic acid strands can also hybridize to form non-Watson-Crick base pairs by so-called "wobble" interactions in which G (guanine) pairs with U (uracil), or alternatively, I (inosine) pairs with C (cytosine), U (uracil) or A (adenine), but with lower binding energies than the normal Watson-Crick base pairing interactions.

The term "identifiable sequence" or "detectable sequence" means a nucleotide sequence which can be detected by hybridization and/or PCR technology by a primer or probe designed for specific interaction with the target nucleotide sequence to be identified. The interaction of the target nucleotide sequence with the specific probe or primer can be detected by optical and/or visual means to determine the presence of the target nucleotide sequence.

In one embodiment, the invention present provides a method by which DNA and fluorophore can be bound to various substrates. With this method DNA can be bound to materials, resist all kinds of finishing processes, such as washing and cleaning, and yet be safely retrieved in order to authenticate the product. Authentication can occur by several methods. One method involves adding fluorophore to the product, making rapid identification possible, as a UV light could detect the presence of a fluorophore. Another authentication method involves binding DNA to substrates via a chemical linker. A linker often includes a chain of carbon atoms with a reactive functional group at the end. This reactive functional group can be activated to bind covalently to an available group or to the substrate or the product to be marked. This DNA attached to the product is unique to the particular product and therefore acts as its fingerprint, making authentication possible. These methods combined would create a fool proof method of identification, where the fluorescence of the product would be the first level of protection and the DNA would be the second, unique and definite layer that could not be duplicated.

In one embodiment the invention provides botanical DNA markers, SigNature™ DNA (Applied DNA Sciences, Stony Brook, N.Y.) that essentially cannot be copied, and are resistant to various chemical and textile treatments. To ensure adherence, SigNature™ DNA was formulated to be tightly bound to both natural and synthetic fibers and other amorphous material such as wool, cotton, polyesters, such as for instance, nylon and polyethylene terephthalate (PET). These textile fabrics can be marked with SigNature™ DNA during the manufacturing process circumventing the need for any additional steps in marking textiles products. As a proof of concept, various woolen yarns and fabrics were finished using standard protocols and the survivability of the SigNature™ DNA was examined at the point of sale as described in the Examples below. In all textiles tested, SigNature™ DNA was recovered and the products were forensically authenticated. Thus, marking textile products with SigNature™ DNA can provide an economical, reliable, and secure method for marking, branding, and forensically authenticating textile products at the DNA level.

Embodiments of the present invention are listed below as non-limiting examples illustrating the invention, but are not intended to be taken as limits to the scope of the present invention, which will be immediately apparent to those of skill in the art.

Exemplary embodiments provide methods for increasing the recoverability of a taggant from an object without disturbing the appearance of the object. Several exemplary embodiments of the present invention are described in detail below.

Exemplary embodiments of the present invention also provide methods for authenticating an object using taggants that have been incorporated onto an object or into a liquid for binding of an activated DNA taggant.

For example, an exemplary embodiment of the invention provides a method for increasing the recoverability of a taggant from an object; the method includes incorporating a DNA taggant onto the surface of an object or into a liquid for binding of the activated DNA taggant to an object or surface.

Alkali Metals

The alkali metals are members of Group I in the periodic table consisting of the elements lithium (Li), sodium (Na), potassium (K), rubidium (Rb), cesium (Cs) and francium (Fr). These alkali metals of the periodic table are elements that exhibit homologous chemical characteristics.

The members of the alkali metals of group I elements of the periodic table are arranged in a series according to their electronic configurations, which are responsible for their chemical characteristics.

The chemistry of each of the first five members of the alkali metals of group I: lithium (Li), sodium (Na), potassium (K), rubidium (Rb) and cesium (Cs) is well established. The chemistry of francium is not well established as extra precautions must be taken due to its radioactivity and so its properties have been less well characterized.

TABLE I

Atomic structure of the alkali metals of group I

| ATOMIC NO. | ELEMENT | ELECTRONS/SHELL |
|---|---|---|
| 3 | Lithium (Li) | 2, 1 |
| 11 | Sodium (Na) | 2, 8, 1 |
| 19 | Potassium (K) | 2, 8, 8, 1 |
| 37 | Rubidium (Rb) | 2, 8, 18, 8, 1 |
| 55 | Cesium (Cs) | 2, 8, 18, 18, 8, 1 |
| 87 | Francium (Fr) | 2, 8, 18, 32, 18, 8, 1 |

The atomic number corresponds to the number of protons per nucleus, and is equal to the total number of electrons in the electron shells.

The alkali metals also react with water to form strongly alkaline hydroxides and should be handled with great care. The alkali metals have the lowest first ionization energies in their respective periods of the periodic table because of their low and the ability to attain a noble gas configuration by losing just one electron. The second ionization energy of all of the alkali metals is very high as it is in a full shell that is also closer to the nucleus; thus, they almost always lose a single electron, forming cations.

The chemistry of lithium shows several differences from that of the rest of the group as the $Li^+$ cation is small and polarizes its counter-charged anions, giving its compounds a more covalent character. Lithium hydroxide is the only alkali metal hydroxide that is not deliquescent. Francium is also predicted show some differences due to its high atomic weight, causing its electrons to travel at considerable fractions of the speed of light and making relativistic effects more prominent. Whereas the electronegativities and ionization energies of the alkali metals decrease in the series from lithium to cesium, the electronegativity and ionization energy of the last alkali metal, francium are calculated to be slightly higher than those of cesium due to the stabilization of the 7 s electrons; and the relative atomic radii of the cesium and francium atoms.

The hydroxide anion has the chemical formula: $OH^-$. It consists of an oxygen atom and a hydrogen atom held together by a covalent bond, and carries a negative electric charge. It is an important constituent of water. It functions as a base, as a ligand, a nucleophile, and a catalyst. The hydroxide ion forms salts, some of which dissociate in aqueous solution, liberating solvated hydroxide ions.

In organic chemistry, the hydroxide ion can act as a catalyst or as a nucleophilic reagent. An hydroxyl (OH) group, is present in alcohols, phenols, carboxylic acids and related functional groups.

Water is at equilibrium with its component ions:

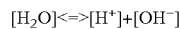
[$H_2O$]<=>[$H^+$]+[$OH^-$]

Water contains a concentration of $10^{-7}$ M [$H^+$] ions. This is expressed as water having a pH of 7.0 on the logarithmic scale.

Strong alkalis are almost completely dissociated. Thus, the strong alkali, sodium hydroxide is essentially completely dissociated in an aqueous solution.

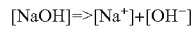
[NaOH]=>[$Na^+$]+[$OH^-$]

Water is only partly dissociated and has a fixed dissociation constant K according to the formula:

$$K = \frac{[H^+] \times [OH^-]}{[H_2O]}$$

Thus, an increase in the concentration of the $OH^-$ ion forces the lowering of the concentration of $H^+$ ions, by covalent binding to produce water molecules. Using this formula the concentration of [$H^+$] and thus the pH of a sodium hydroxide solution can be readily estimated:

1.0 M NaOH contains $10^{-14}$ M [$H^+$] ions, i.e. has a pH of 14.0;

0.1 M NaOH contains $10^{-13}$ M [$H^+$] ions, i.e. has a pH of 13.0;

0.01 M NaOH contains $10^{-12}$ M [$H^+$] ions, i.e. has a pH of 12.0;

0.001 M NaOH contains $10^{-11}$ M [$H^+$] ions, i.e. has a pH of 11.0;

0.0001 M NaOH contains $10^{-10}$ M [$H^+$] ions, i.e. has a pH of 10.0;

0.00001 M NaOH contains $10^{-9}$ M [$H^+$] ions, i.e. has a pH of 9.0; and so on.

Alkaline extraction of DNA from cells of organisms takes advantage of the alkali-stable nature of DNA. Cell membranes are disrupted by treatment with alkali, releasing the cellular contents, and melting the double-stranded the nuclear and mitochondrial DNA to release the single stranded DNA forms. These DNA strands readily re-hybridize, snapping back to their double stranded helical structure that can be isolated from the alkali-treated cellular milieu.

The inventors have surprisingly discovered that alkali treatment of isolated DNA also activates the DNA for covalent binding. Without wishing to be bound by theory, it is believed that alkaline conditions lead to ionization of the free hydroxyls at the 3' ends of the DNA strands. The negatively charged —$O^-$ group produced at the 3' end of the DNA is a strong nucleophile, reactive with positively charged groups to form stable covalent bonds, stably binding the DNA.

The invention provides methods of binding of a deoxyribonucleic acid to a substrate: The method includes exposing the deoxyribonucleic acid to alkaline conditions, and contacting the deoxyribonucleic acid to the substrate. The DNA bound to the substrate is available for binding by hybridization probes, PCR amplification and DNA sequencing methods.

In one embodiment, the alkaline conditions are produced by mixing the deoxyribonucleic acid with an alkaline solution having a high pH, for instance the pH of the alkaline solution can be a pH of about 9.0 or higher; a pH of about 10.0 or higher; a pH of about 11.0 or higher, or even a pH of about 12.0 or higher, and contacting the deoxyribonucleic acid that has been exposed to the alkaline conditions with the substrate. In one embodiment, the alkaline solution is a solution of a hydroxide of an alkali metal.

Another embodiment of the present invention provides a method of binding a deoxyribonucleic acid to a substrate, the method including exposing the deoxyribonucleic acid to alkaline conditions, wherein the alkaline conditions are produced by mixing the deoxyribonucleic acid with an alkaline solution, and contacting the deoxyribonucleic acid that has been exposed to the alkaline conditions with the substrate; wherein the alkaline solution is a solution of a hydroxide of an alkali metal and the alkali metal is selected from the group consisting of lithium (Li), sodium (Na), rubidium (Rb), and cesium (Cs).

Another embodiment of the present invention provides a method of binding a deoxyribonucleic acid to a substrate, the method including exposing the deoxyribonucleic acid to alkaline conditions, wherein the alkaline conditions are produced by mixing the deoxyribonucleic acid with an alkaline solution, and contacting the deoxyribonucleic acid that has been exposed to the alkaline conditions with the substrate; wherein the alkaline solution is a solution of an alkali metal hydroxide, wherein the alkali metal hydroxide is selected from the group consisting of lithium hydroxide (LiOH), sodium hydroxide (NaOH) and cesium hydroxide (CsOH). In one embodiment, the alkali metal hydroxide is sodium hydroxide (NaOH).

Another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with a solution of an alkali metal hydroxide, wherein the alkali metal hydroxide solution having a concentration of from about 1 mM to about 1.0 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of from about 10 mM to about 0.9 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of from about 0.1 M to about 0.8 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of from about 0.4 M to about 0.8 M.

Another embodiment the invention provides a method of binding a deoxyribonucleic acid to a substrate, the method including exposing the deoxyribonucleic acid to alkaline conditions and contacting the deoxyribonucleic acid that has been exposed to the alkaline conditions with the substrate; wherein the alkaline conditions are produced by mixing the deoxyribonucleic acid with a solution of an alkali metal hydroxide, the alkali metal hydroxide solution having a concentration of about 0.6 M.

Another embodiment of the present invention provides a method of binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9.0 to about 14.0 and incubated at a temperature of from about 0° C. to about 65° C. to produce the alkaline conditions.

Another embodiment of the present invention provides a method of binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9.0 to about 14.0 and incubated at a temperature of from about 5° C. to about 55° C. to produce the alkaline conditions.

Another embodiment of the present invention provides a method of increasing binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9 to about 14 and incubated at a temperature of from about 10° C. to about 45° C. to produce the alkaline conditions.

Another embodiment of the present invention provides a method of increasing binding of a deoxyribonucleic acid to a substrate, wherein the method includes exposing the deoxyribonucleic acid to alkaline conditions and contacting the alkaline exposed deoxyribonucleic acid to the substrate, wherein the deoxyribonucleic acid is mixed with an alkaline solution having a pH from about 9 to about 14 and incubated at a temperature of from about 15° C. to about 35° C. to produce the alkaline conditions.

Another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with a solution of an alkali metal hydroxide and incubating the mixture at a temperature of from about 0° C. to about 65° C.

Another embodiment of the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with a solution of an alkali metal hydroxide and incubating the mixture at a temperature of from about 15° C. to about 22° C.

In another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of from about 0.1 M to about 1.0 M and incubating the mixture for a period of from about 1 minute to about 6 hours at a temperature of from about 10° C. to about 45° C.

In another embodiment the invention provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of from about 0.1 M to about 1.0 M and incubating the mixture for a period of from about 1 minute to about 6 hours at a temperature of from about 15° C. to about 25° C. to produce the alkaline conditions.

Another embodiment provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of about 0.6 M and incubating the mixture for a period of from about 1 minute to about 6 hours at a temperature of from about 15° C. to about 35° C.

Another embodiment provides a method of binding a deoxyribonucleic acid to a substrate, the method including exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution having concentration of about 0.6 M and incubating the mixture for a period of from about 10 minutes to about 2 hours at a temperature of from about 18° C. to about 22° C. to produce the alkaline conditions.

In one embodiment, the present invention provides a method of binding a deoxyribonucleic acid to a substrate, the method includes exposing the deoxyribonucleic acid to alkaline conditions, wherein the alkaline conditions are produced by mixing the deoxyribonucleic acid with an alkaline solution having a high pH, incubating the mixture and then neutralizing the alkaline solution and contacting the neutralized solution containing the deoxyribonucleic acid that has been exposed to the alkaline conditions with the substrate. In one embodiment, the alkaline solution is a solution of a hydroxide of an alkali metal selected from the group consisting of lithium (Li), sodium (Na), rubidium (Rb), and cesium (Cs).

In another embodiment the present invention provides a method of binding a deoxyribonucleic acid to a substrate, the method includes exposing the deoxyribonucleic acid to alkaline conditions, and contacting the deoxyribonucleic acid that has been exposed to the alkaline conditions with the substrate; wherein the alkaline conditions are produced by mixing the deoxyribonucleic acid with an alkali metal hydroxide solution, and adding a molar excess of a polyionic polymer.

The polyionic polymer can be any suitable polyionic polymer. In one embodiment the polyanionic polymer is a polyamino acid. The polyamino acid can be a homopolymer of a natural amino acid such as L-lysine, or a homopolymer of a non-naturally occurring amino acid, such as for instance D-lysine. In one embodiment, the polyamino acid homopolymer is selected from the group consisting of polyputrescine, polycadaverine, polyspermidine, and polylysine.

Alternatively, in another embodiment, deoxyribonucleic acid can be mixed with a solution of any suitable high pH buffer to produce the alkaline conditions. The high pH buffer can be any suitable high pH buffer with a pKa in a range of from about 9.0 to about 11.0 or higher. In an embodiment, the pH of the high pH buffer can be, for example, a pH of about 9.0 or higher; a pH of about 10.0 or higher; or a pH of about 11.0 or higher. For example, in another embodiment, deoxyribonucleic acid can be mixed with a suitable high pH buffer such as CABS (4-[cyclohexylamino]-1-butanesulphonic acid) with a useful pH range of about 10.0-11.4 (at 25° C.) and a pKa of about 10.70 (at 25° C.) Product No. C5580 Sigma Aldrich, St. Louis, Mo.; CAPS (N-cyclohexyl-3-aminopropanesulfonic acid) with a useful pH range of about 9.7-11.1 (at 25° C.), a pKa of about 10.56 (at 20° C.), a pKa of about 10.40 (at 25° C.) and a pKa of about 10.02 (at 37° C.) Sigma Aldrich Product Nos. C6070 and C2632; AMP (2-amino-2-methyl-1-propanol) with a useful pH range of about 9.0-10.5 (at 25° C.), a pKa of about 9.70 (at 25° C.) Sigma Aldrich Product Nos. A9199 and A9879; CAPS 0 (N-cyclohexyl-2-hydroxyl-3-aminopropanesulfonic acid) with a useful pH range of about 8.9-10.3 (at 25° C.), a pKa of about 9.60 (at 25° C.), a pKa of about 9.43 (at 37° C.) Sigma Aldrich Product Nos. C2278 and C8085; CHES (2-(N cyclohexylamino)ethanesulphonic acid) with a useful pH range of about 8.60-10.0 (at 25° C.), a pKa of about 9.55 (at 20° C.), a pKa of about 9.49 (at 25° C.) and a pKa of about 9.36 (at 37° C.) Sigma Aldrich Product Nos. C2885 and C8210; AMPSO (3-[(1,1-dimethyl-2-hydroxyethyl)amino]-2-hydroxypropanesulfonic acid) with a useful pH range of about 8.3-9.7 (at 25° C.), a pKa of about 9.00 (at 25° C.), a pKa of about 9.10 (at 37° C.) Sigma Aldrich Product Nos. A6659 and A7585, to produce the alkaline conditions.

In an exemplary embodiment of the present invention, the deoxyribonucleic acid that has been exposed to the alkaline conditions is added as a component of a liquid composition. The liquid composition any be any suitable liquid composition, such as for instance, a printing ink. For example, in one embodiment, the ink may be a heat-curing epoxy-acrylate ink, such as Product No. 4408R or the 970 series Touch Dry® pellet each from Markem®, Keene, N.H. Alternatively, the Artistri® P5000+Series-Pigment Ink from Dupont®, or an Epoxy Acrylate Ink, such as Product No. 00-988, from Rahn USA Corp. can be used.

The taggants of the present invention include, for example, nucleic acid taggants. Nucleic acid is a general term for deoxyribonucleic acid (DNA) or ribonucleic acid (RNA), and can be synthetic, or derived from an animal, a plant, a bacterium, a virus, a fungus, or a synthetic vector or a fragment of any of the above-listed nucleic acids, etc. It should be noted that a synthetic nucleic acid can have a sequence of a naturally occurring nucleic acid of an animal, plant, bacterium, fungus, virus or any other organism or synthetic vector. Alternatively, a synthetic nucleic acid can have a unique sequence not found in nature. It should be understood that such unique non-natural sequences may have stretches of sequences which are found in nature, but the entire non-natural sequence is unique and is not found in any plant, animal or virus or any other natural organism. In particular, the nucleic acid sequence encoding the element of data or indicia encrypted or encoded in the taggant of the invention is a unique, non-natural sequence and thereby is adapted for use in authentication of an object of interest.

The taggant useful in combination with the bound DNA that has been activated by alkaline treatment according to the present invention can be any suitable detectable or traceable taggant, for example, a chemical marker or a biological marker. In an embodiment of the methods of the present invention, the taggant is selected from a UV fluorophore, a ceramic IR marker, other DNA, an amino acid, a peptide, a protein, a lipid, a sugar, a polysaccharide, a pheromone, a scent, a trace element, a rare earth element, or a combination of any two or more thereof.

In an embodiment of the present invention, the taggant includes a nucleic acid. In one embodiment, the taggant consists essentially of DNA and no other significant component useful for identification or authentication.

Alternatively, or in addition, other taggants such as, for example, ultraviolet (UV) taggants, Up Converting Phosphor (UCP) infrared (IR) taggants, UV marker taggants, UV fluorophore taggants, ceramic IR marker taggants, protein taggants, and/or trace element taggants can be used in combination with deoxyribonucleic acid taggants activated by alkaline treatment according to the methods of the present invention. In an exemplary embodiment, the taggants used may include, for example, a combination of DNA taggants, and an IR upconverting phosphor (UCP) taggant. In another exemplary embodiment, the taggants used may include, for example, a combination of DNA taggants, an IR upconverting phosphor (UCP) taggant and a UV taggant. For example, in an exemplary embodiment, the IR (UCP) taggant can be, for example, a green, a blue or a red (UCP) IR taggant, such as for instance the Green IR Marker, Product No. BPP-1069; the Blue UCP, Product No. BPP-1070; or the Red UCP, Product No. BPP-1071 from Boston Applied Technologies Inc., Woburn, Mass.

The solution in which the soluble taggants are dissolved according to the methods of the present invention can include, for example, water, TE buffer (10 mM Tris-HCl, 1 mM EDTA), Tris-glycine buffer, Tris-NaCl buffer, TBE buffer (Tris-borate-EDTA), TAE buffer (Tris-acetate-EDTA) and TBS buffer (Tris-buffered saline), HEPES buffer (N-(2-Hydroxyethyl)piperazine-N'-ethanesulfonic acid), MOPS buffer (3-(N-Morpholino)propanesulfonic acid), PIPES buffer (Piperazine-N,N'-bis(2-ethanesulfonic acid), MES buffer (2-(N-Morpholino)ethanesulfonic acid), PBS (Phosphate Buffered Saline), PBP buffer (sodium phosphate+EDTA), TEN buffer (Tris/EDTA/NaCl), TBST buffer (Tris-HCl, NaCl, and Tween 20), PBST buffer (Phosphate Buffered Saline with Tween 20) and any of the many other known buffers used in the biological and chemical sciences.

The objects of interest marked with the deoxyribonucleic acid and optional additional taggants according to exemplary embodiments of the present invention include, for example, ceramic surfaces, plastic films, vinyl sheets, antiques, items of jewelry, identification cards, credit cards, magnetic strip cards, paintings, artwork, souvenirs, sports collectibles and other collectibles. The authenticity of these objects can then be verified by identifying the taggants bound or covalently bonded thereon through, for example, methods described in further detail below.

In one embodiment, the surface to which the deoxyribonucleic acid that has been exposed to alkaline conditions is bound can be the surface of an object or item formed of a polymer, such as a polymer selected from the group consisting of polycarbonate (PC), polymethyl methacrylate (PMMA), polyurethane (PU), polystyrene (PS), nylon or polypropylene (PP) all of which are readily commercially available.

In one embodiment, the method of the present invention further includes binding an object with the deoxyribonucleic acid that has been exposed to alkaline conditions according to the methods of the present invention, the deoxyribonucleic acid such that the activated deoxyribonucleic acid is chemically bonded to the object, thereby providing the object with authentication, tracking and anti-counterfeiting functions.

The deoxyribonucleic acid that has been exposed to alkaline conditions that has been applied onto an object provides a traceable deoxyribonucleic acid taggant. The traceable deoxyribonucleic acid taggant can be applied over all or part of the object to be identified, validated, authenticated, or if the object is an item of commerce, the item can be tracked at any point through the stream of commerce.

In another embodiment, the traceable deoxyribonucleic acid is an alkaline pH activated DNA bound to the object.

In another embodiment, the alkaline pH activated DNA is bound to an object including a material selected from the group consisting of cotton, wool, nylon, plastic, metal, glass, wood, printing ink, and a pharmaceutical powder.

In another embodiment, the alkaline pH activated DNA is bound to a plastic material selected from the group consisting of a polycarbonate (PC), a polymethyl methacrylate (PMMA), a polyurethane (PU), a polystyrene (PS), a polyamide, a polypropylene (PP), a polyvinyl chloride (PVC), polysulphone, polyvinilacetate (PVA), polyester (PES), a polyethylene terephthalate (PET), a polyethylene (PE), a benzocyclobutene (BCB), a high-density polyethylene (HDPE), a polyvinylidene chloride (PVDC), a low-density polyethylene (LDPE), a high impact polystyrene (HIPS), an acrylonitrile butadiene styrene (ABS), a phenol formaldehyde resin (PF), a melamine formaldehyde (MF), a polyetheretherketone (PEEK), a polyetherimide (PEI), polyimide (PI), a polyether ketone imide, a polylactic acid (PLA), a polytetrafluoroethylene (PTFE), a polymethyl pentene (PMP), a polyether ketone (PEK), a polyether sulfone (PES), a polyphenylene sulfide (PPS), a polytetrafluoroethylene (PTFE), a fluropolymer, a silicone, an Ionomer, a moldable elastomer, an ethylene vinyl alcohol (EVOH), a methalocene polymer and a polyethylene naphthalate material.

In one embodiment, the object marked with the traceable deoxyribonucleic acid includes a pharmaceutical composition comprising a pharmaceutical tablet, a pharmaceutical capsule, or a pharmaceutical powder.

Another exemplary embodiment of the present invention provides a method for authenticating an object which includes providing an object to which a taggant is bound or covalently bonded, sampling the object for identification, tracking, or verifying the authenticity of the object by identifying the unique traceable deoxyribonucleic acid (DNA) taggant. In one embodiment, the unique taggant is a DNA taggant having a unique DNA sequence and the unique DNA sequence is stored in a database that matches the unique DNA sequence to the data elements corresponding to the object which is bound to or covalently bonded to the unique taggant. The database can in turn be located on a computer that can be accessed in order to locate, track, authenticate and verify the identity of the tagged object from which the taggant was detected.

DNA taggants useful in the examples described below include any suitable DNA taggant, such as for instance, in one embodiment, the DNA taggant is a double stranded DNA oligomer having a length of between about 40 base pairs and about 1000 base pairs. In other embodiments the DNA taggant is a double stranded DNA oligomer with a length of between about 80 and 500 base pairs. In another embodiment the DNA taggant is a double stranded DNA oligomer having a length of between about 100 and about 250 base pairs. Alternatively, the DNA taggant can be single-stranded DNA or any suitable length, such as between about 40 bases and about 1000 bases; between about 80 and 500 bases; or between about 100 and about 250 bases. The DNA taggant can be natural DNA, whether isolated from natural sources or synthetic; or the DNA taggant can be a synthetically produced non-natural sequence. All or a portion of the DNA may comprise an identifiable sequence.

In one exemplary embodiment, the DNA taggant is identifiable by any suitable detection and/or identification method such as for example, hybridization with a taggant-sequence specific nucleic acid probe, an in situ hybridization method (including fluorescence in situ hybridization: FISH), amplification using a polymerase chain reaction (PCR), such as quantitative/real time PCR and detection of the amplified sequences (amplicons) by any of the variety of standard well known methods.

In another embodiment, the hybridization can be carried out with DNA probes, each having a specific nucleotide sequence capable of hybridizing with its complementary sequence. Different probes may be included, one to each cell or well of an array or matrix so that only the probe having the complement to the DNA taggant will hybridize and generate a detection signal at the unique location of the complementary probe. Alternatively, if the complementary probe is present in several cells of wells arranged in a particular pattern, then hybridization with the complementary DNA taggant sequence will be detected in the precise pattern of the specific probes in the array or matrix. For example, in the PCR identification method, the nucleic acid taggants, e.g., DNA taggants recovered from the object are amplified by polymerase chain reaction (PCR) and resolved by gel electrophoresis. Since the sequence of the nucleic acid taggants of the present invention are unique and specific to the tagged object, the original nucleic acid will be amplified only by use of primers having specific sequences complementary to a portion of the unique taggant sequence. Through this procedure, if the examined object carries the original nucleic acid, the PCR procedure will amplify extracted nucleic acid to produce amplicons of a predetermined size and a sequence identical to a portion of the original nucleic acid sequence of the taggant. In contrast, if the sample recovered from the examined object does not include the unique nucleic acid corresponding to the authentic object, there will likely be no amplified nucleic acid product, or if the primers do amplify the recovered nucleic acid to produce one or more random amplicons, these one or more amplicons cannot have the unique taggant nucleic acid sequence from the authentic object. Furthermore, the random amplicons derived from counterfeit articles are also of random lengths and the likelihood of producing amplicons of the exact lengths specified by the taggant-specific primers is vanishingly small. Therefore, by comparing the sizes of PCR products, the authenticity of labeled objects can be verified, non-authentic objects can be screened and rejected and anti-counterfeit screening purpose is then achieved.

The number of amplicons amplified and the lengths of the amplicons can be determined after any molecular weight or physical dimension-based separation, such as for instance and without limitation, gel electrophoresis in any suitable matrix medium for example in agarose gels, polyacrylamide gels or mixed agarose-polyacrylamide gels and the electrophoretic separation can be in a slab gel or by capillary electrophoresis.

Alternatively, the deoxyribonucleic acid that has been exposed to alkaline conditions that has been bound to the item or surface of interest can be subjected to PCR, the PCR amplicons can be recovered and sequenced according to well known routine nucleic acid sequencing techniques.

EXAMPLES

It should be understood that following examples set forth are intended to be illustrative only and that exemplary embodiments of the present invention are not limited to the conditions or materials recited therein.

The following examples illustrate embodiments of the present invention: The DNA is activated and can then be mixed in any solution or buffer and applied onto the surface to which it is to be bound and thereby marked with the specific alkaline-activated DNA sequence.

Example 1: Alkaline Activation of a DNA Taggant

Fifty microliters of carrier nucleic acid (40 mg/mL in deionized water) containing the double stranded 199 base pair DNA taggant at a concentration of 0.5 mg/L was activated by mixing with 50 uL 0.6 M NaOH solution (EMD Millipore Chemicals, ACS grade) in a disposable snap cap microtube and allowed to stand at room temperature for 30 minutes. The activated nucleic acid mixture was ready for dilution as needed and application to items or articles to be marked.

Example 2: Marking and Authentication of Raw Cotton

To determine the endogenous levels of DNA in Giza cottons cultivar 86 and 88 (Giza 86 and Giza 88), cottons were cleaned of external debris; total DNA was extracted and amplified in a polymerase chain reaction (PCR). The DNA was subsequently analyzed using a standard capillary electrophoresis (CE) following ADNAS proprietary protocols. As expected, ADNAS exogenous marker DNA was not detected in these two samples FIGS. 1 and 2, Panel 1).

In a subsequent experiment, ADNAS exogenous marker DNA (also known as SigNature™ DNA) was formulated, conditioned to bind to textile and was applied onto the raw cotton during the ginning process. The cotton was dried (approximately 30 minutes at room temperature), and then tested by routine DNA detection methods to provide forensic authentication. The ADNAS marker DNA was amplified in a polymerase chain reaction and analyzed using our proprietary methods. SigNature™ DNA was strongly detected in both Giza 86 and Giza 88 (FIGS. 1 and 2, Panel 2). To distinguish between the adsorbed and bound DNA to the cotton, both Giza 86 and Giza 88 were subjected to various water washes, the cotton was dried in an oven and then subjected to a second round of DNA authentication. Despite the vigorous water washes, SigNature™ DNA was recovered from both formulation 1 and formulation 2 (see FIGS. 1 and 2, Panels 3 and 4).

Example 3: Testing Retrieval of DNA after Washes

Giza 86 cotton and Giza 88 cotton were marked with SigNature™ DNA as described above. To determine if the ADNAS marker DNA was bound to the cotton fiber or to the naturally coating wax, the cotton was subjected to sequential washes with chemicals known to dissolve and remove the wax. The first wash consisted of vigorous water rinsing. The second wash consisted of washing the cotton with alcohols with forceful agitation. The third sequential wash consisted of washing the cotton with solvents also with forceful agitations. The ADNAS marker DNA was PCR amplified and analyzed using our proprietary methods. In brief, DNA was detected in all samples after each wash suggesting that ADNAS mark was bound tightly to the cotton fiber proper using formulation 1 (FIGS. 3 and 4). Similar data was obtained with formulation 2 (Data not shown), showing that the marker DNA is not bound to coating wax that is removed by the harsh solvent treatment.

Example 4: Marking and Authentication of Wool Yarn

Figure 6A:
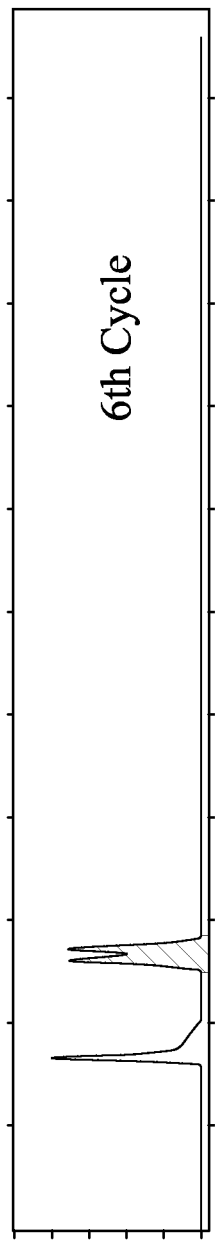
Figure 6B:
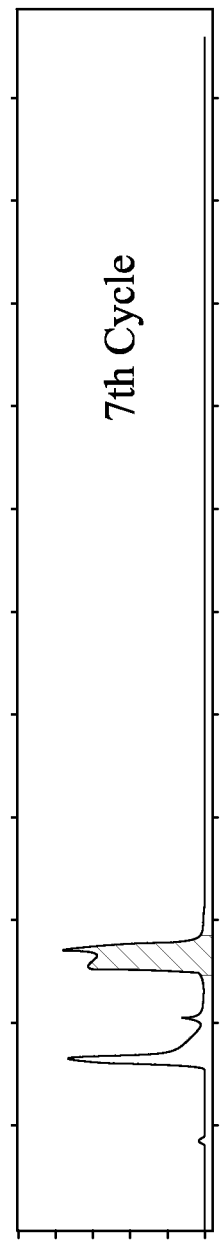

Wool yarn was marked with SigNature™ DNA using a lick-roller. The marked yarn was then woven into a fabric, which was professionally finished. The professional finish consisted of scouring, detergent wash, water rinsing, acid treatment, and finally drying. At the end of the week long finishing process, the fabric was authenticated and SigNature™ DNA was recovered (FIG. 5, panel 1). In parallel, unmarked yarn was also woven and finished according the manufacturer process. This unmarked fabric was subjected to the same testing as the DNA marked fabric. As expected, the SigNature™ DNA was not detected in the unmarked fabric. To further establish that the SigNature™ DNA was permanently bound to the fabric, the finished fabric was dried cleaned 10 times by professional dry cleaners. At the end of each cycle, a sample of the fabric was cut off and authenticated. The SigNature™ DNA was shown to be recovered from all samples. Additionally, the amount of SigNature™ DNA that was recovered was similar if not identical in all samples suggesting that the SigNature™ DNA did not wash off during these stringent series of washes (FIG. 6).

Example 5: Marking and Authentication of Synthetic Fibers

Synthetic threads from nylon and polyesters, like all other amorphous products, are formed by extruding fiber forming material or master batches. The extrusion process requires heating the master batches to a temperature higher than the melting point, and then the material is physically pulled out to form the yarn. The pulled yarn is immediately submerged in a cool water bath. To mark synthetic fibers, master batches of nylon, polyesters and PET were mixed with SigNature™ DNA, extruded, and the SigNature™ formed yarn from polyesters and nylon or the film produced from the PET master batches were authenticated. SigNature™ DNA was recovered from all three products. To ascertain that the recovered DNA was dispersed in the extruded products, yarns from nylon and polyesters as well as the film produced from PET were subjected to vigorous washes, and then SigNature™ DNA was recovered and analyzed per the standard protocols. SigNature™ DNA was recovered from all samples including nylon (FIG. 7A), polyester threads and film made from PET (FIG. 7B), and amplified in the PCR authentication process as described above. A negative control with no SigNature™ DNA added was treated in parallel and showed no amplification peak (FIG. 7C)

Example 6: Inclusion of Alkali Activated DNA with a Printing Ink

DNA is activated as described above in Example 1. Activated DNA is diluted in a standard buffer such as, for instance, TE (Tris.HCL pH 7.4), PBS (Phosphate Buffered Saline), HEPES buffer (N-(2-Hydroxyethyl)piperazine-N'-ethanesulfonic acid), or TBE buffer (Tris-borate-EDTA) and then mixed with the printing ink. The mixture is then paddle blended, printed on an object, item, document, etc. and then cured (e.g. by heating under an high intensity mercury lamp). The cured ink including the DNA is then sampled using a cotton swab with any suitable solvent such as, for instance, MEK, EtOH, MEK, ether, or acetone or any suitable aqueous buffer such as, for instance, TE (Tris.HCL pH 7.4), PBS (Phosphate Buffered Saline), HEPES buffer (N-(2-Hydroxyethyl)piperazine-N'-ethanesulfonic acid), or TBE buffer (Tris-borate-EDTA) and swabbed across the printed surface. A sample of the DNA is obtained by the swab, and the DNA is then authenticated by a standard PCR procedure as described above.

Example 7: Inclusion of Alkali Activated DNA into Pharmaceutical Powders

DNA is activated as described above in Example 1. Activated DNA is diluted in a standard buffer such as, for instance, TE (Tris.HCL pH 7.4), PBS (Phosphate Buffered Saline), HEPES buffer (N-(2-Hydroxyethyl)piperazine-N'-ethanesulfonic acid), or TBE buffer (Tris-borate-EDTA) and then mixed with a powder that includes a mixture of an active pharmaceutical composition and one or more excipients. The powder including the activated DNA is then dried by any suitable method such as, for instance, heating in an air stream. The DNA associated with the dried powder is retrieved for authentication by sampling the dried powder, and mixing the sample of the dried powder with any suitable solvent such as, for instance, MEK, EtOH, MEK, ether, or acetone or any suitable aqueous buffer such as, for instance, TE (Tris.HCL pH 7.4), PBS (Phosphate Buffered Saline), HEPES buffer (N-(2-Hydroxyethyl)piperazine-N'-ethanesulfonic acid), or TBE buffer (Tris-borate-EDTA). The DNA retrieved is then authenticated by a standard PCR procedure as described above.

Example 8: Compression of the DNA Coated Powder into Tablets

The dried powder including the activated DNA solution prepared as in Example 4 is compressed into a tablet. The DNA is retrieved for authentication by, for instance, scraping, cutting, abrading, or gouging a portion of the tablet to collect a sample. The DNA sample collected from the tablet is then authenticated by a standard PCR procedure as described above.

Example 9: Coating of the Activated DNA onto Pharmaceutical Tablets

DNA is activated as described above in Example 1. Activated DNA is diluted in a standard buffer such as, TE (Tris.HCL pH 7.4), PBS (Phosphate Buffered Saline), HEPES buffer (N-(2 Hydroxyethyl)piperazine-N'-ethanesulfonic acid), or TBE buffer (Tris-borate-EDTA) and then coated onto a tablet including active substances and excipients. The coated tablet including the activated DNA is then dried by any suitable method such as, for instance, heating in an air stream. The DNA is obtained by, for instance, scraping, cutting, abrading, or gouging a portion of the tablet. Alternatively, the DNA is obtained for authentication by swabbing the tablet with a swab moistened with any suitable solvent such as, for instance, MEK, EtOH, MEK, ether, or acetone or any suitable aqueous buffer such as, for instance, TE (Tris.HCL pH 7.4), PBS (Phosphate Buffered Saline), HEPES buffer (N-(2-Hydroxyethyl)piperazine-N'-ethanesulfonic acid), or TBE buffer (Tris-borate-EDTA). In another alternative, the DNA is obtained for authentication by wiping the tablet with a cloth moistened with a suitable solvent or a suitable buffer such as, for instance, those already mentioned above in this example. The DNA sample collected from the tablet is then authenticated by a PCR procedure as described above.

Example 10: Inclusion of the Activated DNA with Pharmaceutical Capsules

The powder including the activated DNA solution prepared in Example 4 is then encapsulated in a capsule. The DNA in the capsule is retrieved for authentication by puncturing or cutting open the capsule and sampling the powder therein, and mixing the sample of the powder with any suitable solvent such as, for instance, MEK, EtOH, MEK, ether, or acetone or any suitable aqueous buffer such as, for instance, TE (Tris.HCL pH 7.4), PBS (Phosphate Buffered Saline), HEPES buffer (N-(2-Hydroxyethyl)piperazine-N'- ethanesulfonic acid), or TBE buffer (Tris-borate-EDTA). The DNA retrieved from the capsule is then authenticated by performing a standard PCR procedure as described above.

Example 11: Inclusion of Alkali Activated DNA with Indentifying Indicia

DNA is activated as described above in Example 1. Activated DNA is diluted in a standard buffer such as, for instance, TE (Tris.HCL pH 7.4), PBS (Phosphate Buffered Saline), HEPES buffer (N-(2-Hydroxyethyl)piperazine-N'-ethanesulfonic acid), or TBE buffer (Tris-borate-EDTA) and applied to an identifying indicia (e.g., a label, logo or badge affixed to an item) by spraying the DNA solution on the identifying indicia. Alternatively, the DNA solution is applied to the identifying indicia by soaking the identifying indicia in the DNA solution. The coating on the identifying indicia including the DNA is then dried by a suitable method such as, for instance, heating under a heat lamp, or drying in an air stream. The DNA in the identifying indicia is retrieved for authentication by swabbing the identifying indicia with a swab moistened with any suitable solvent such as, for instance, MEK, EtOH, MEK, ether, or acetone or any suitable aqueous buffer such as, for instance, TE (Tris.HCL pH 7.4), PBS (Phosphate Buffered Saline), HEPES buffer (N-(2-Hydroxyethyl)piperazine-N'-ethanesulfonic acid), or TBE buffer (Tris-borate-EDTA). The DNA is retrieved from the identifying indicia and authenticated by soaking the identifying indicia in a suitable solvent or a suitable buffer such as, for instance, those already mentioned above in this example. Alternatively, the DNA is collected from the indicia by scraping, cutting, abrading, or gouging a portion of the identifying indicia to collect a sample. The retrieved DNA is then authenticated by performing a standard PCR procedure as described above.

The full scope of the invention will be appreciated in view of the U.S. Patents and references cited in this specification, the entire disclosures if which are hereby incorporated by reference.

Having described exemplary embodiments of the present invention, it is further noted that it will be readily apparent to those of reasonable skill in the art that various modifications may be made without departing from the spirit and scope of the invention which is defined by the metes and bounds of the appended claims.

What is claimed is:

1. A method of binding a deoxyribonucleic acid to the surface of a non-metal substrate which is not nylon or plastic, the method comprising:
   providing a deoxyribonucleic acid;
   exposing the deoxyribonucleic acid to an alkaline metal hydroxide solution comprising an alkali metal hydroxide at a concentration in a range from about 0.1M to about 1.0 M and incubating the mixture for from about 1 minute to about 6 hours at a temperature of from about 15° C. to about 25° C. to produce an alkaline-treated deoxyribonucleic acid, wherein the alkaline metal hydroxide solution is selected from the group consisting of lithium hydroxide, sodium hydroxide and cesium hydroxide; and
   contacting the alkaline treated deoxyribonucleic acid to the surface of the non-metal substrate, for a period of time sufficient for the alkaline-treated deoxyribonucleic acid to covalently bind to the surface of the non-metal substrate.

2. A method of binding a deoxyribonucleic acid to the surface of a non-metal substrate which is not nylon or plastic, the method comprising:
   providing a deoxyribonucleic acid;
   exposing the deoxyribonucleic acid to an alkaline metal hydroxide solution comprising an alkali metal hydroxide at a concentration of about 0.6M and incubating the mixture for from about 10 minutes to about 2 hours at a temperature of from about 18° C. to about 22° C. to produce an alkaline-treated deoxyribonucleic acid, wherein the alkaline metal hydroxide solution is sodium hydroxide; and
   contacting the alkaline treated deoxyribonucleic acid to the surface of the non-metal substrate, for a period of time sufficient for the alkaline-treated deoxyribonucleic acid to covalently bind to the surface of the non-metal substrate.

3. The method of claim 1, wherein the non-metal substrate is selected from the group consisting of cotton, wool, glass, wood, printing ink, and a pharmaceutical composition.

4. The method of claim 2, wherein the non-metal substrate is selected from the group consisting of cotton, wool, glass, wood, printing ink, and a pharmaceutical composition.

* * * * *